United States Patent
Noh et al.

(10) Patent No.: US 10,094,811 B2
(45) Date of Patent: Oct. 9, 2018

(54) COLOR CHANGEABLE HYDROGEN DETECTION SENSOR BASED ON MOLYBDENUM OXIDE AND METHOD OF MANUFACTURING THE SAME

(71) Applicants: Hyundai Motor Company, Seoul (KR); Kia Motors Corporation, Seoul (KR); Ajou University Industry-Academic Cooperation Foundation, Suwon, Gyeonggi-Do (KR)

(72) Inventors: Yong Gyu Noh, Gyeonggi-do (KR); Ho June Bae, Seoul (KR); Hyung Tak Seo, Seoul (KR); Shankara S. Kalanur, Gyeonggi-do (KR); Yeong An Lee, Gyeongsangnam-do (KR)

(73) Assignees: Hyundai Motor Company, Seoul (KR); Kia Motors Corporation, Seoul (KR); Ajou University Industry-Academic Cooperation Foundation, Suwon, Gyeonggi-do (KR)

(*) Notice: Subject to any disclaimer, the term of this patent is extended or adjusted under 35 U.S.C. 154(b) by 7 days.

(21) Appl. No.: 15/277,067

(22) Filed: Sep. 27, 2016

(65) Prior Publication Data

US 2017/0191970 A1    Jul. 6, 2017

(30) Foreign Application Priority Data

Dec. 30, 2015  (KR) ........................ 10-2015-0189651

(51) Int. Cl.
  *G01N 33/00*    (2006.01)
  *G01N 21/78*    (2006.01)
  (Continued)

(52) U.S. Cl.
  CPC ......... *G01N 33/005* (2013.01); *G01N 21/783* (2013.01); *G01N 27/304* (2013.01);
  (Continued)

(58) Field of Classification Search
  CPC .... G01N 33/005; G01N 21/783; G01N 31/10; G01N 27/304; G01N 31/22;
  (Continued)

(56) References Cited

U.S. PATENT DOCUMENTS

| | | | | | |
|---|---|---|---|---|---|
| 4,046,852 | A | * | 9/1977 | Vertes | C01G 39/00 423/58 |
| 4,579,751 | A | * | 4/1986 | Forster | G01N 27/125 338/34 |

(Continued)

FOREIGN PATENT DOCUMENTS

| | | |
|---|---|---|
| KR | 2009-0115324 A | 11/2009 |
| KR | 10-2013-0057475 A | 5/2013 |

(Continued)

OTHER PUBLICATIONS

Hamagami, Jun-ichi et al., "Preparation and characterization of an optically detectable H2 gas sensor consisting of Pd/MoO3 thin films", Sensors and Actuators B, 13-14 (1993) pp. 281-283.

*Primary Examiner* — Lore R Jarrett
(74) *Attorney, Agent, or Firm* — Mintz Levin Cohn Ferris Glovsky and Popeo, P.C.; Peter F. Corless

(57) ABSTRACT

Disclosed are a hydrogen detection sensor and a method of manufacturing the same. The hydrogen detection sensor is manufactured by using hydrothermal synthesis method to synthesize a molybdenum oxide ($MoO_3$) nanostructure, and irradiating UV light thereon to form an $MoO_3$—Pd nanocomposite comprising the molybdenum oxide nanostructure with palladium (Pd) catalyst particles, and coating the $MoO_3$—Pd nanocomposite on a substrate. As such, a visible (Continued)

color change from the MoO₃ before and after exposure to hydrogen may be so obvious that the sensing or sensitivity of hydrogen and the long-term stability may be substantially improved. In addition, the manufacturing process is simple, and the manufacturing costs may be reduced.

11 Claims, 9 Drawing Sheets

(51) Int. Cl.
    *G01N 27/30*     (2006.01)
    *G01N 31/10*     (2006.01)
    *G01N 31/22*     (2006.01)

(52) U.S. Cl.
    CPC .............. *G01N 31/10* (2013.01); *G01N 31/22* (2013.01); *G01N 31/224* (2013.01)

(58) Field of Classification Search
    CPC ............... G01N 33/0013; G01N 33/52; G01N 33/54346; G01N 31/224; Y10T 436/22; Y10T 442/2033; Y10T 442/20; Y10T 442/2508; Y10T 436/214; Y10T 436/205831; Y10T 436/216; B82Y 30/00; D01F 1/04; D01F 1/10
    See application file for complete search history.

(56) References Cited

U.S. PATENT DOCUMENTS

| | | | |
|---|---|---|---|
| 8,268,392 B1 * | 9/2012 | Muradov | ............... B82Y 30/00 422/86 |
| 2005/0054869 A1 * | 3/2005 | Lugmair | ............... B01J 23/002 558/323 |
| 2007/0251822 A1 * | 11/2007 | Hoagland | ............ G01N 33/005 204/424 |
| 2009/0090626 A1 | 4/2009 | Holt et al. | |

FOREIGN PATENT DOCUMENTS

| | | |
|---|---|---|
| KR | 2013-0093306 A | 8/2013 |
| KR | 2014-0134174 A | 11/2014 |
| KR | 10-1557611 B1 | 10/2015 |

* cited by examiner

COLOR CHANGEABLE HYDROGEN DETECTION SENSOR BASED ON MOLYBDENUM OXIDE AND METHOD OF MANUFACTURING THE SAME

CROSS-REFERENCE TO RELATED APPLICATION

This application claims under 35 U.S.C. § 119(a) the benefit of Korean Patent Application No. 10-2015-0189651 filed on Dec. 30, 2015, the entire contents of which are incorporated herein by reference.

TECHNICAL FIELD

The present invention relates to a hydrogen detection sensor that may change its color upon hydrogen exposure and a method of manufacturing the same. The hydrogen detection sensor may be manufactured by performing a hydrothermal synthesis method to synthesize a molybdenum oxide ($MoO_3$) nanostructure, irradiating UV light to the molybdenum oxide nanostructure and palladium catalyst to form an $MoO_3$—Pd nanocomposite and forming a coating layer for the hydrogen detection sensor by coating the $MoO_3$—Pd nanocomposite on a substrate. As such, due to the molybdenum oxide, color change before and after the exposure to hydrogen may be visibly so obvious that the sensing or sensitivity of hydrogen and the long-term stability of the hydrogen detection sensor may be substantially improved. In addition, the manufacturing process may be simple, and the manufacturing costs may be reduced.

BACKGROUND

Hydrogen is a future clean energy, and has been applied in various fields such as process industries, fuel cells, and separation and storage of hydrogen. Since there is a danger of ignition or explosion when hydrogen is present at a concentration of 4% or greater in the air, a hydrogen detection sensor may be a very important factor for safety. In particular, since hydrogen has a high diffusion rate and the detection of hydrogen is easily affected by environmental conditions, it is an appropriate safety strategy to provide as many sensors as possible by using inexpensive sensors.

Recently, studies on a hydrogen sensor using a metal oxide of $WO_3$ have been conducted. For example, a nanocomposite particle sensor using $WO_3$ nanoparticles has been synthesized and the nanoparticles are so small that the contact area of a catalyst reduced by hydrogen in the air with $WO_3$ can be greatly increased. This sensor method may be used as a chemochromic sensor in which colors are changed without an external power source under the hydrogen exposure conditions. However, in the hydrogen sensor using $WO_3$, the reaction efficiency and reliability of the sensor may deteriorate over time as the ability of the catalyst particles to decompose hydrogen molecules into atoms by reacting with oxygen or water steam in the external environment rapidly may decline over time.

Therefore, there is a need for developing a new detection sensor which is inexpensive and produced by a simple process, and secures durability without adversely affecting the sensitivity and responsiveness of the sensor.

The above information disclosed in this Background section is only for enhancement of understanding of the background of the invention and therefore it may contain information that does not form the prior art that is already known in this country to a person of ordinary skill in the art.

SUMMARY OF THE INVENTION

In preferred aspects, the present invention provide a hydrogen detection sensor that may visibly and obviously change color or discolor before and after the present invention is exposed to hydrogen such that the sensing or sensitivity of hydrogen and the long-term stability may be substantially improved. In addition, the process of manufacturing the hydrogen detection sensor may be simple, and thus the manufacturing costs may be reduced. For example, the hydrogen sensor may be produced by steps comprising: performing a hydrothermal synthesis method to synthesize a molybdenum oxide ($MoO_3$) nanostructure and irradiating UV light to the molybdenum oxide nanostructure and palladium catalyst to form an $MoO_3$—Pd nanocomposite comprising the molybdenum oxide nanostructure and palladium (Pd) catalyst particles, and forming a coating layer for the hydrogen sensor by coating the $MoO_3$—Pd nanocomposite on a substrate.

The term "nanostructure" refers to a structure or an object having a size (e.g. cross sectional size, diameter or a length) in nanometer scale. For example, the nanostructure of the molybdenum oxide ($MoO_3$) in the present invention suitably may have a size of about 1 to 900 nm, of about 10 to 500 nm, or particularly of about 20 to 100 nm in diameter. In addition, the shape of the nanostructure may be formed in spherical particle, rod, tube, polygonal particles or the like, but not be particularly limited. For example, the nanostructure of the molybdenum oxide ($MoO_3$) in the present invention suitably may have a rod-like shape (nanorod) having a diameter in a range of nanometer scale (e.g. 2 to 100 nm) while having a length in micrometers, e.g. from about 1 to about 100 μm. Alternatively, the nanostructure of the molybdenum oxide ($MoO_3$) may have a plate-like shape (nanoplate).

The term "nanocomposite" refers to a material comprising two or more materials that may have different properties or phases as combined and may have a size range (e.g. cross sectional size, diameter or a length) in nanometer scale. For example, the nanocomposite may comprise the molybdenum oxide ($MoO_3$) and the palladium catalyst particles, each component suitably may have a size in nanometer scale.

In one aspect, the present invention provides a hydrogen detection sensor that may change its color or be discolored upon exposure to hydrogen with molybdenum oxide, which is excellent in the sensing or sensitivity of hydrogen. The hydrogen detection sensor comprising molybdenum oxide.

The hydrogen detection sensor may comprise a substrate; and a coating layer formed on a surface of the substrate and discolored when exposed to hydrogen. Particularly, the coating layer for the hydrogen sensor may comprise a molybdenum oxide (MoO3)-Pd nanocomposite in which palladium (Pd) catalyst particles may be adsorbed on an molybdenum oxide (MoO3) nanostructure.

Preferably, the substrate may be selected from the group consisting of a paper filter, a glass substrate, a polymer film, ink, pigment, and paint.

The molybdenum oxide ($MoO_3$) nanostructure suitably may have a length of about 1 to 100 μm and a diameter of about 20 to 100 nm.

The palladium (Pd) catalyst particles suitably may have an average particle diameter of about 3 to 15 nm.

The coating layer suitably may have a coating thickness of about 0.1 to 200 μm. In another aspect, the present invention provides a method of manufacturing a hydrogen detection sensor comprising molybdenum oxide thereby improving long-term stability. The method may comprise providing a substrate; forming a molybdenum oxide nanostructure; preparing a palladium catalyst solution by mixing a polymer with a palladium precursor solution; forming an $MoO_3$—Pd nanocomposite by mixing the molybdenum oxide nanostructure with the palladium catalyst solution, and irradiating UV light to the mixture; and forming a coating layer by coating the $MoO_3$—Pd nanocomposite on the substrate.

The molybdenum oxide nanostructure may be suitably prepared by steps comprising: preparing an aqueous molybdenum oxide solution by mixing an acid solution with an aqueous molybdenum ammonium solution; forming the molybdenum oxide nanostructure by hydrothermally synthesizing the aqueous molybdenum oxide solution; and heat-treating the molybdenum oxide nanostructure.

The molybdenum oxide nanostructure suitably may be formed at a temperature of about 140 to 180° C. for about 2 to 6 hours.

The molybdenum oxide nanostructure suitably may be heat-treated at a temperature of about 400 to 600° C. for about 1 to 3 hours.

The polymer suitably may be polyvinylpyrrolidone, polyvinyl alcohol, or a mixture thereof.

Further provided is a vehicle comprising the hydrogen detection sensor as described herein.

Other aspects and preferred embodiments of the invention are discussed infra.

A hydrogen detection sensor that may change color or be discolored due to molybdenum oxide according to the present invention may be substantially improved in the sensing or sensitivity of hydrogen and the long-term stability, can be produced by a simple process. For example, a molybdenum oxide ($MoO_3$) nanostructure may be produced using a hydrothermal synthesis, and irradiated UV lights thereon to form a coating layer for a hydrogen sensor to form an $MoO_3$—Pd nanocomposite comprising the molybdenum oxide nanostructure and palladium (Pd) catalyst particles.

Accordingly, the manufacturing costs may be reduced because a visible color change of the sensor before and after exposure to hydrogen may be so obvious.

BRIEF DESCRIPTION OF THE DRAWINGS

The above and other features of the present invention will now be described in detail with reference to certain exemplary embodiments thereof illustrated in the accompanying drawings which are given hereinbelow by way of illustration only, and thus are not limitative of the present invention, and wherein.

Figure 1:
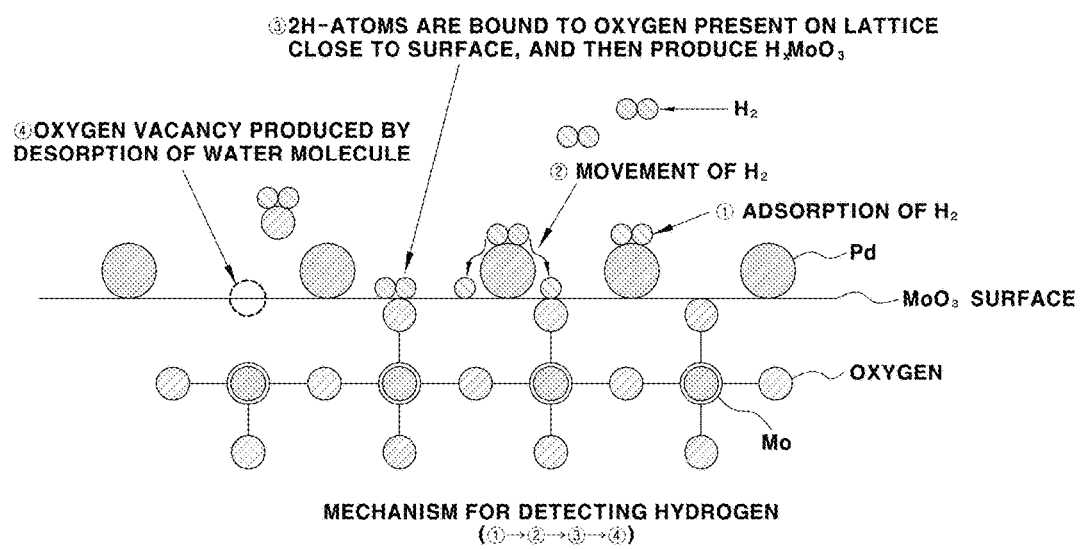
FIG. 1 illustrates a mechanism for detecting hydrogen of an exemplary hydrogen detection sensor according to an exemplary embodiment of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The terminology used herein is for the purpose of describing particular exemplary embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g.

fuels derived from resources other than petroleum). As referred to herein, a hybrid vehicle is a vehicle that has two or more sources of power, for example both gasoline-powered and electric-powered vehicles.

Hereinafter, the present invention will be described in more detail through one exemplary embodiment.

The present invention provides a hydrogen detection sensor may change color or be discolored due to molybdenum oxide.

Such "color change" or "discoloration" may be visibly observed by naked eyes on a surface of the discoloration material. In preferred embodiment, the "discoloration" or "chemical discoloration" may refer to a change in visibly detectable colors which is induced by chemical reaction such as reduction, oxidation and the like, with the hydrogen. That is, there would be a visible color change (as detected with naked eyes) of the sulfide layer between 1) before the hydrogen detection sensor comprising molybdenum oxide is exposed to the hydrogen; and 2) at least about 1 second, about 5 seconds, about 10 seconds, about 20 seconds, about 30 seconds, about 40 seconds, about 50 seconds, or about 60 seconds after the hydrogen detection sensor is exposed to the hydrogen. Further, the "color change" or "discoloration" may be visibly detected with naked eyes when the discoloration material, i.e. molybdenum oxide, in the hydrogen detection sensor in an amount of about 1 wt %, about 2%, about 3 wt %, about 4 wt %, about 5 wt %, about 7 wt %, about 10 wt %, about 15 wt %, about 20 wt %, about 25 wt %, about 30 wt %, about 35 wt %, about 40 wt %, about 50 wt %, about 60 wt %, about 70 wt %, about 80 wt %, about 90 wt %, about 99 wt %, or about 100 wt % based on the total weight thereof is chemically reacted with the hydrogen.

The hydrogen detection sensor may comprise a substrate and a coating layer formed on a surface of the substrate. Preferably, the coating layer for detecting hydrogen may comprise a molybdenum oxide ($MoO_3$)—Pd nanocomposite in which the palladium (Pd) catalyst particles may be adsorbed on the $MoO_3$ nanostructure.

FIG. 1 illustrates a mechanism for detecting hydrogen of the hydrogen detection sensor according to an exemplary embodiment of the present invention. The coating layer for the hydrogen sensor may comprise an $MoO_3$—Pd nanocomposite. When the $MoO_3$—Pd nanocomposite, in which the Pd catalyst is adsorbed on the surface of the $MoO_3$ nanostructure, is exposed to the hydrogen atmosphere, hydrogen may be adsorbed on the surface of the Pd catalyst. The hydrogen molecules adsorbed on the surface of the Pd catalyst may be dissociated into hydrogen atoms.

The dissociated hydrogen atoms may move to the surface of the $MoO_3$ nanostructure, and then may permeate into the $MoO_3$ nanostructure. In this manner, two hydrogen atoms permeating into the lattice of the $MoO_3$ nanostructure react with oxygen to produce a localized water molecule, and produce oxygen vacancies. These reactions may promote oxygen ions and Mo ions to be displaced from the original position. The oxidation state of Mo may be reduced from +6 to +5 (meaning that an extra electron remains). The hydrogen reacted with oxygen partially may reduce the $MoO_3$ nanostructure, and may produce $H_xMoO_3$ (x is a natural number). When the continuous flow of the hydrogen gas, the above reaction may occur. Meanwhile, when hydrogen is removed or discontinued, $MoO_3$ may be bound to oxygen, and thus may return to the original state.

Figure 2:
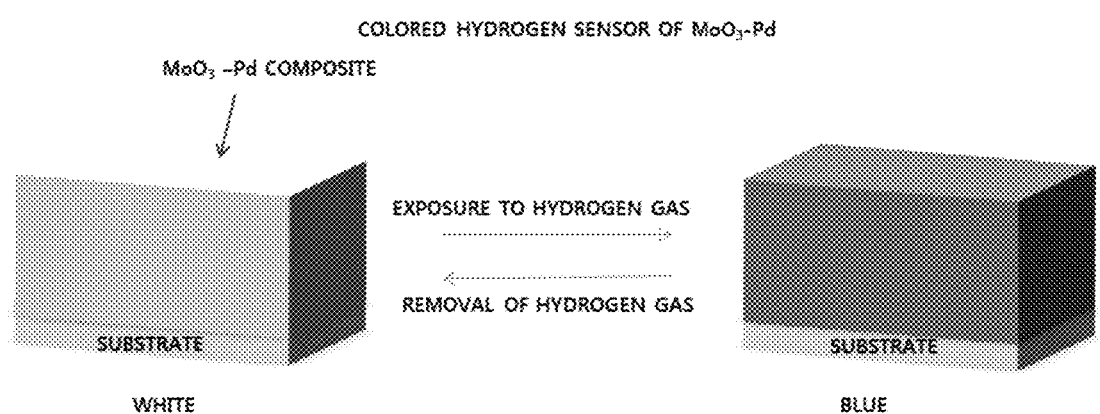
FIG. 2 illustrates a method for detecting hydrogen of an exemplary hydrogen detection sensor according to an exemplary embodiment of the present invention.

FIG. 2 illustrates an exemplary method for detecting hydrogen of the hydrogen detection sensor according to an exemplary embodiment of the present invention. In FIG. 2, the hydrogen detection sensor may have a structure in which a coating layer for detecting hydrogen may be formed on a sensor substrate. In particular, the coating layer may comprise an $MoO_3$—Pd nanocomposite. The hydrogen detection sensor may have white color before being exposed to a hydrogen gas, and as being exposed to a hydrogen gas, the coating layer. Then, the coating layer may return to the original white color when the hydrogen gas is removed. The hydrogen detection sensor may be substantially improved and effective for sensing hydrogen because the visible difference in color change is clearly exhibited before and after the sensor is exposed to hydrogen.

The molybdenum oxide nanostructure suitably may be in the form of a nanorod or nanoplate. In the molybdenum oxide nanostructure, palladium particles may be adsorbed on the surface of the structure by physical or chemical bond. Preferably, the nanostructure may be in the form of a nanorod or nanoplate.

In preferred exemplary embodiments of the present invention, the substrate may be one selected from the group consisting of a paper filter, a glass substrate, a polymer film, ink, pigment, and paint, but the substrate is not limited thereto. For example, when the substrate is the paper filter, the glass substrate, and the polymer film, the $MoO_3$—Pd nanocomposite may be dissolved in a solvent, and then a coating layer for a hydrogen sensor may be formed on the sensor substrate (a paper filter, a glass substrate, or a polymer film). Further, when the substrate is ink, pigment, and paint, the $MoO_3$—Pd nanocomposite may be mixed with a polymer or an aerogel, and then a coating layer for a hydrogen sensor may be formed on the sensor substrate (ink, pigment, or paint).

In preferred exemplary embodiments of the present invention, the molybdenum oxide ($MoO_3$) nanostructure may have a length of about 1 to 100 μm and a diameter of about 20 to 100 nm. The molybdenum oxide ($MoO_3$) is a metal oxide having white color, and may be characterized by having a color change into blue when being exposed to hydrogen. In addition, the molybdenum oxide ($MoO_3$) may reversibly change colors, and thus again may return to white color when hydrogen is removed, tends to have a relatively slow speed of returning to white color, and thus may be characterized by having intermediate properties between reversible and irreversible properties. Furthermore, molybdenum oxide may be relatively inexpensive and relatively less toxic than $TiO_2$ or sulfide-based compounds, and may provide an advantage of simple and rapid synthesis process.

When the diameter of the molybdenum oxide ($MoO_3$) nanostructure is less than about 20 nm, it may be very difficult to control the nanostructure during the particle process, and when the diameter is greater than about 100 nm, the surface area may be decreased, and thus performance may deteriorate when the nanostructure is exposed to hydrogen. In addition, when the length of the molybdenum oxide ($MoO_3$) nanostructure is less than about 1 μm, the productivity may be reduced during the manufacturing process, and when the length is greater than about 100 μm, the performance may deteriorate.

The palladium (Pd) catalyst particles suitably may have an average particle diameter of about 3 to 15 nm. The palladium catalyst may dissociate hydrogen molecules, and diffuse the dissociated hydrogen molecules into molybdenum oxide. Furthermore, when the average particle diameter of the palladium catalyst particles is less than about 3 nm, the durability of the sensor deteriorates and the palladium catalyst particles may be rarely deposited (adsorbed) on molybdenum oxide, and when the average particle diameter is greater than about 15 nm, the hydrogen molecule dissociation performance may deteriorate.

The amount of palladium (Pd) catalyst particles adsorbed suitably may be about 0.1 to 10 μg/cm². When the amount of palladium (Pd) catalyst particles adsorbed is less than about 0.1 μg/cm², the sensitivity performance of the detection sensor may be poor. When the amount is greater than about 10 μg/cm², the manufacturing costs may increase due to the expensive palladium catalyst.

The molybdenum oxide nanostructure and the palladium catalyst catalysts suitably may be mixed at a weight ratio of about 100:0.5 to 100:10. When the mixing ratio is less than about 100:0.5, the sensing performance of the detection sensor may be reduced, and when the mixing ratio is greater than about 100:10, the expensive palladium catalyst may be consumed in a large amount.

The $MoO_3$—Pd nanocomposite may be blue transparent characteristics, and thus a change in color may be easily and effectively recognized while the sensor is exposed to hydrogen. The $MoO_3$—Pd nanocomposite may be mixed with a polymer or an aerogel, and thus may be applied to pigment or paint, and may also be utilized as an electrical-type sensor or an optical-type sensor in addition to a color changeable hydrogen sensor.

The coating layer for a hydrogen sensor suitably may have a coating thickness of about 0.1 to 200 μm. When the thickness of the coating layer for a hydrogen sensor is less than about 0.1 μm, change in color may not be effectively detected or sensed, and when the thickness is greater than about 200 μm, nanoparticles may be consumed in large amounts, and thus the production costs may increase.

The method of manufacturing a hydrogen detection sensor using molybdenum oxide according to an exemplary embodiment the present invention may include: providing a substrate; forming a molybdenum oxide nanostructure; preparing a palladium catalyst solution after mixing a polymer with a palladium precursor solution; forming an $MoO_3$—Pd nanocomposite by mixing the molybdenum oxide nanostructure with the palladium catalyst solution and then irradiating UV light to the mixture; and forming a coating layer for a hydrogen sensor by coating the $MoO_3$—Pd nanocomposite on the substrate.

The molybdenum oxide nanostructure may be formed by steps comprising: preparing an aqueous molybdenum oxide solution by mixing an acid solution with an aqueous molybdenum ammonium solution; forming the molybdenum oxide nanostructure by hydrothermally synthesizing the aqueous molybdenum oxide solution; and heat-treating the molybdenum oxide nanostructure.

The hydrothermal synthesis for forming the molybdenum oxide nanostructure may be carried out at a temperature of about 140 to 180° C. for about 2 to 6 hours. When the temperature of the hydrothermal synthesis is less than about 140° C., the growth of the molybdenum oxide nanostructure may deteriorate, and when the temperature is greater than about 180° C., the reaction may be excessively carried out, and thus it is difficult to adjust the particle size of the molybdenum oxide nanostructure. Preferably, the hydrothermal synthesis may be carried out at a temperature of about 160° C. for 4 hours.

The heat treatment of the molybdenum oxide nanostructure may be carried out at a temperature of about 400 to 600° C. for about 1 to 3 hours. When the temperature of the heat treatment is less than about 400° C., the growth of the molybdenum oxide nanostructure may deteriorate, and when the temperature is greater than about 600° C., the reaction may be excessively carried out, and thus it is difficult to adjust the particle size of the molybdenum oxide nanostructure. Preferably, the heat treatment may be carried out at a temperature of about 500° C. for about 2 hours.

The polymer suitably may include polyvinylpyrrolidone, polyvinyl alcohol, or a mixture thereof during preparing the palladium catalyst solution. The polymer may be a protective film which may minimize the effects of oxygen and moisture, and may be selectively optimized for hydrogen, and thus may enhance the reliability, stability and service life of the sensor without degrading the sensitivity. Furthermore, the polymer, may be a surfactant, such that the uniformity may be improved by adjusting the sizes of the palladium catalyst particles according to the amount of polymer used, and uniformly dispersing the particles.

The molybdenum oxide nanostructure solution may be produced by mixing a solvent with the molybdenum oxide nanostructure in the manufacturing of the $MoO_3$—Pd nanocomposite, and then may be mixed with the palladium catalyst solution. Further, the irradiating of UV light, for example, having a wavelength of about 200 nm to 600 nm, may be carried out for about 1 to 5 minutes, and preferably for about 3 minutes.

The spin coating method suitably may be performed in the forming of the coating layer, particularly for forming a thin coating layer on the sensor substrate.

Therefore, the hydrogen detection sensor including molybdenum oxide according to various exemplary embodiments of the present invention may have be manufactured by using the hydrothermal synthesis to synthesize the molybdenum oxide ($MoO_3$) nanostructure and irradiating UV lights to the nanostructure to form the $MoO_3$—Pd nanocomposite comprising the molybdenum oxide nanostructure and the palladium (Pd) catalyst particles, and coating the $MoO_3$—Pd nanocomposite on the substrate. As such, the hydrogen detection sensor of the present invention may have improved sensing or sensitivity of hydrogen and the long-term stability, and can be produced by a simple process, thereby reducing the manufacturing costs. Particularly, a visible color change before and after the sensor is exposed to hydrogen may be obvious due to the molybdenum oxide changing color upon hydrogen exposure.

EXAMPLES

Hereinafter, the present invention will be described in more detail with reference to the Examples, and the present invention is not limited by the following Examples.

Preparation Example 1: Manufacture of $MoO_3$ Nanostructure

An aqueous molybdenum ammonium solution was produced by mixing 100 ml of water with 1 g of molybdenum ammonium (($NH_4$)$_2MoO_4$). And then, 5 ml of concentrated $HNO_3$ was added to the aqueous solution, and then the resulting mixture was mixed for 1 hour. And then, the aqueous molybdenum ammonium solution, in which hydrochloric acid is mixed, was placed into an autoclave, and a molybdenum ammonium nanostructure precipitate was obtained by performing a hydrothermal synthesis at a temperature of 160° C. for 4 hours. The autoclave was cooled to normal temperature to wash and dry the precipitate. As a result, a crystalline $MoO_3$ nanostructure was obtained by subjecting the precipitate to heat treatment at a temperature of 500° C. for 2 hours.

Figure 3A:
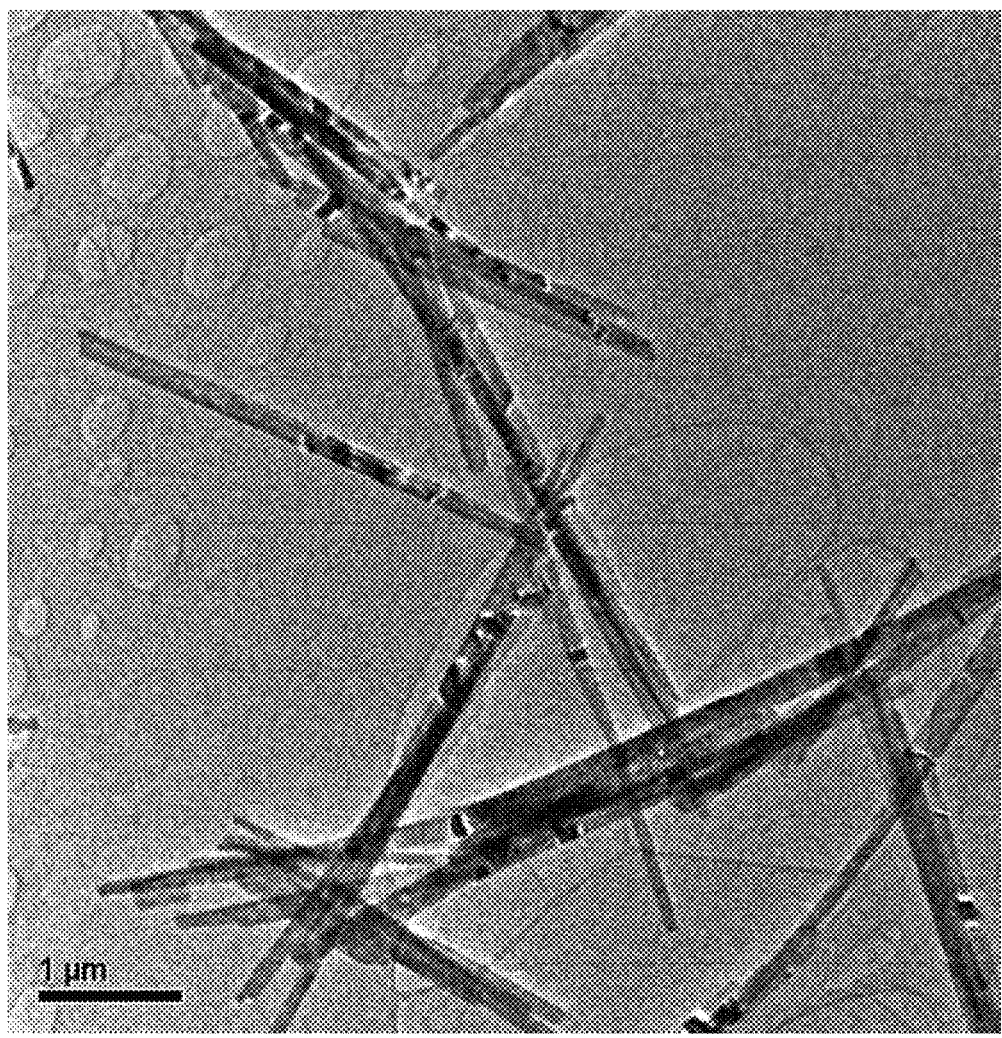
FIGS. 3A-3B are transmission electron microscope (TEM) images of an exemplary $MoO_3$ nanostructure according to an exemplary embodiment of the present invention, where, in FIG. 3A, exemplary $MoO_3$ nanostructures are shown in micrometer-scale and in FIG. 3B, exemplary $MoO_3$ nanostructure are shown in nanometer-scale.
Figure 3B:
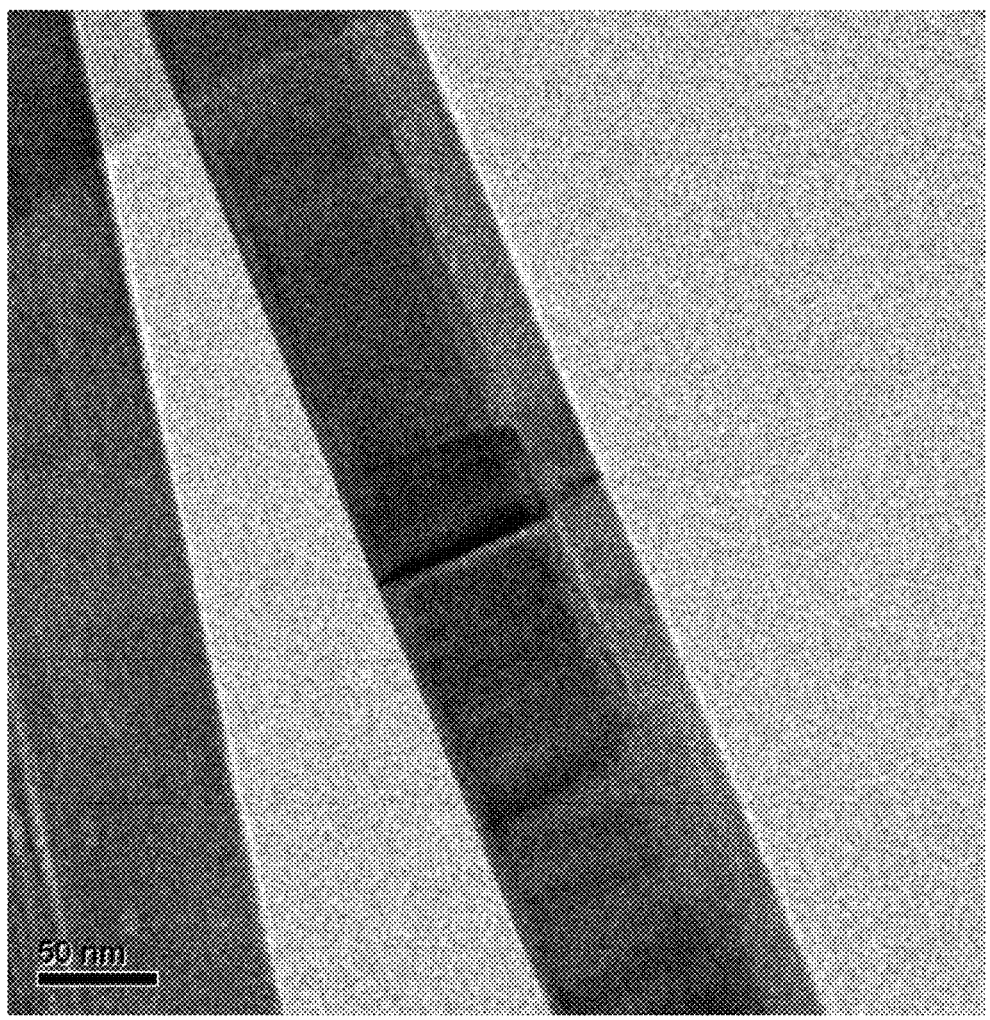

FIG. 3A-3B are transmission electron microscope (TEM) images of an exemplary $MoO_3$ nanostructure manufactured in Preparation Example 1. In FIG. 3A, it was confirmed that the average length of the $MoO_3$ nanostructure was 10 to 20 μm, and in FIG. 3B, it was shown that the average diameter of the $MoO_3$ nanostructure was 5 to 10 nm.

Preparation Example 2: Manufacture of $MoO_3$—Pd Nanocomposite

A palladium catalyst solution was produced by mixing 6 mg of $PdCl_2$ with 20 ml of methanol, mixing 20 mg of polyvinylpyrrolidone with the resulting mixture, and then performing an ultrasonic treatment for 2 hours. An $MoO_3$ nanostructure solution was produced by mixing 30 ml of methanol with 100 mg of the $MoO_3$ nanostructure obtained through Preparation Example 1. An $MoO_3$—Pd nanocomposite was obtained by mixing 20 ml of the palladium catalyst solution with 30 ml of the $MoO_3$ nanostructure solution, and then irradiating UV light thereon for 3 minutes. The obtained composite was filtered and dried. In this case, in the composite, the solution was grey color.

Figure 4:
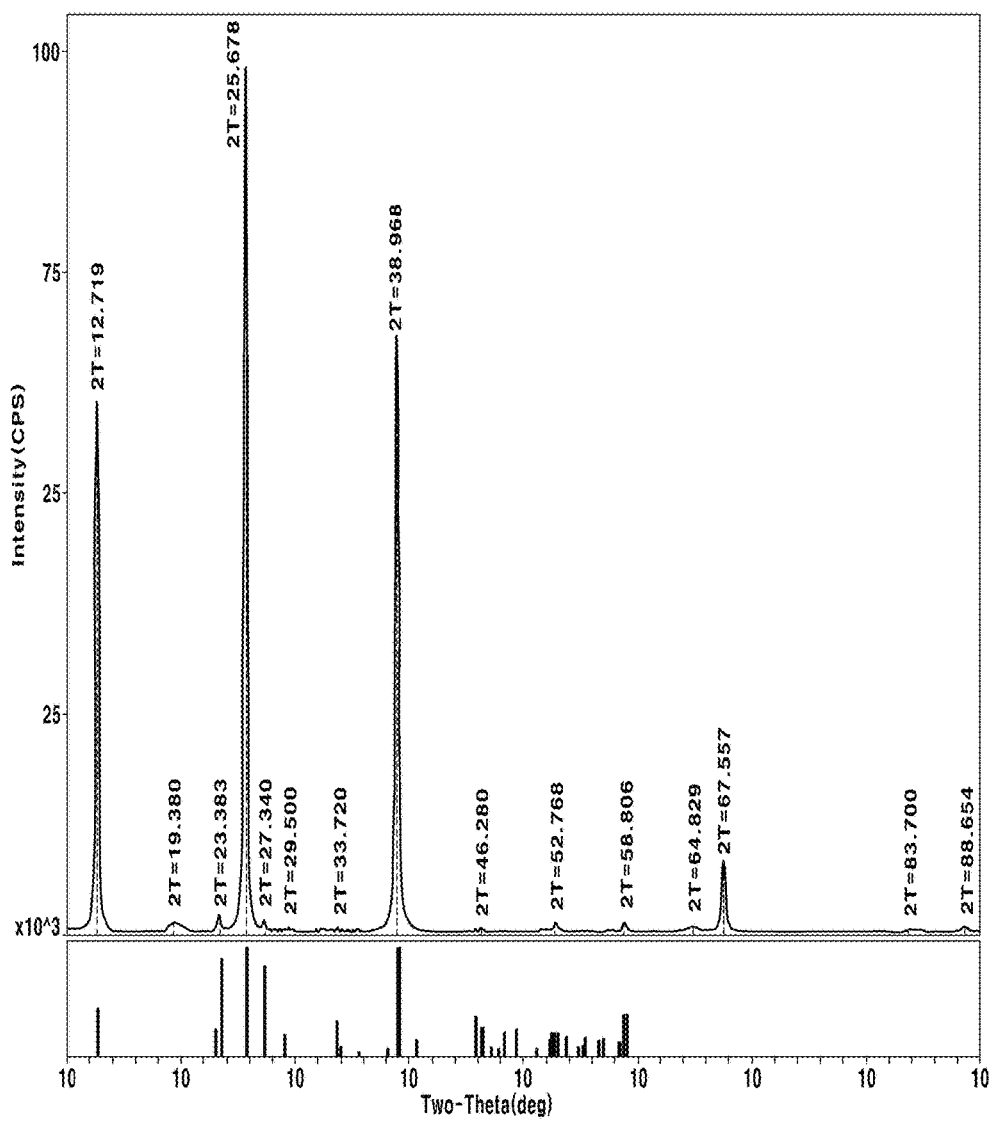
FIG. 4 is an X-ray diffraction analysis (XRD) image of an exemplary $MoO_3$—Pd nanocomposite according to an exemplary embodiment of the present invention.

FIG. 4 is an X-ray diffraction analysis (XRD) image of the $MoO_3$—Pd nanocomposite manufactured in Preparation Example 2. In FIG. 4, it was observed that each of the peaks of the crystallized $MoO_3$ nanostructure and the palladium catalyst particles was observed, and through the observation, it could be seen that the crystallized $MoO_3$ nanostructure was bound to the palladium catalyst particles.

Figure 5:
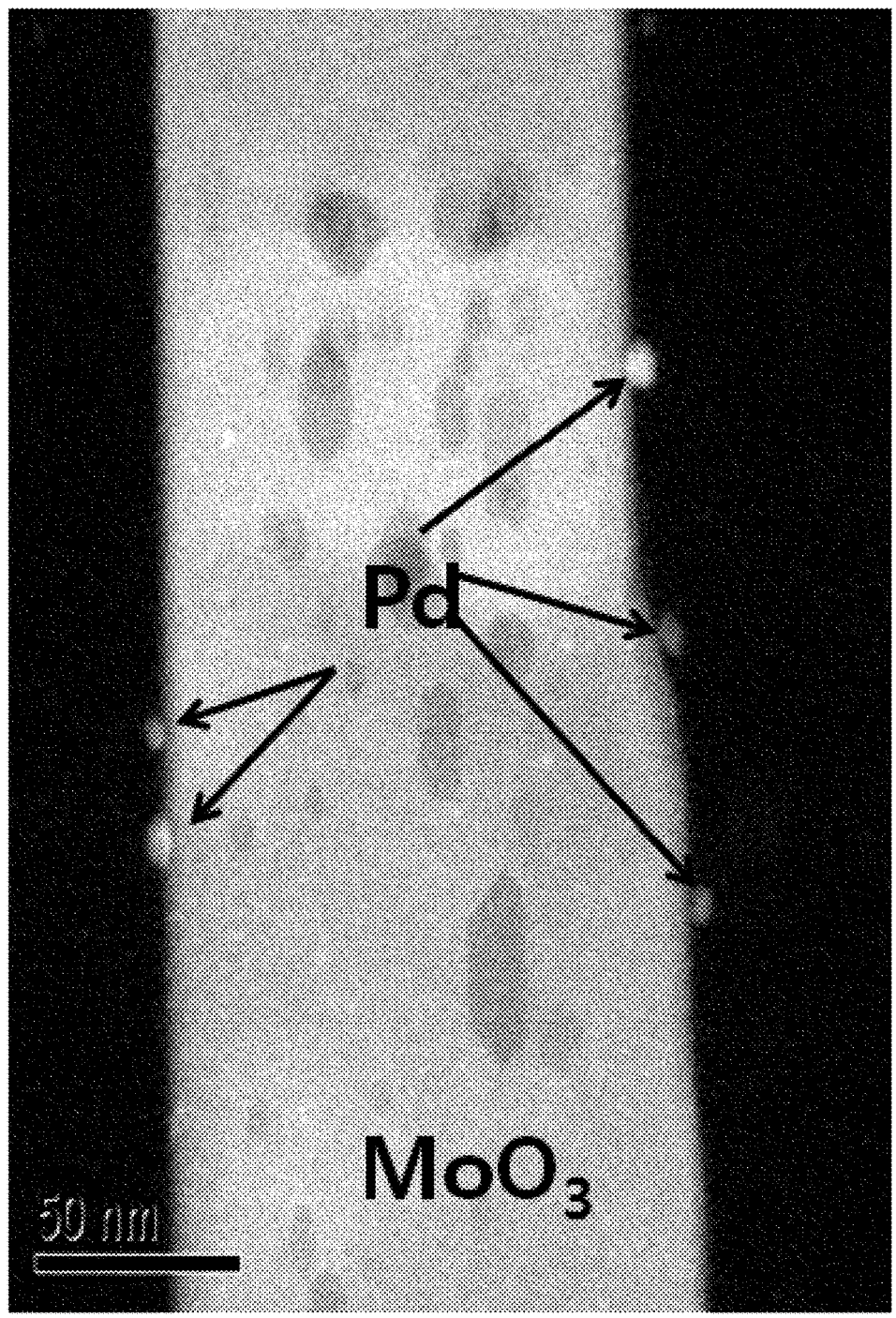
FIG. 5 is a transmission electron microscope (TEM) image of an exemplary $MoO_3$—Pd nanocomposite according to an exemplary embodiment of the present invention.

FIG. 5 is a transmission electron microscope (TEM) image of the $MoO_3$—Pd nanocomposite manufactured in Preparation Example 2. In FIG. 5, it could be confirmed that Pd catalyst particles were adsorbed on the surface of the $MoO_3$ nanostructure. It could be confirmed that palladium catalyst particles with a size of several nanometers were deposited on the $MoO_3$ nanostructure. Further, since the palladium catalyst particles were deposited in the form of particles which did not agglomerate, the surface area which could be brought into contact with hydrogen molecules was significantly increased, and through the increase in surface area, the efficiency of change in color may be increased as a whole.

Example 1

As the sensor substrate, a paper filter was provided. In addition, an $MoO_3$—Pd nanocomposite solution was produced by adding 10 ml of methanol to 100 mg of the $MoO_3$—Pd nanocomposite manufactured in Preparation Example 2, and then performing ultrasonic treatment for 1 hour. Subsequently, 10 ml of the $MoO_3$—Pd nanocomposite solution was applied onto the paper filter, and then spin coating was performed at 1,500 rpm for 30 seconds. The paper filter was dried at a temperature of 60° C. for 4 hours. As a result, a color changeable hydrogen detection sensor was manufactured by using an electron beam to form a coating layer for a hydrogen sensor, which was composed of an $MoO_3$—Pd nanostructure having a thickness of 100 μm on the paper filter.

Example 2

A color changeable hydrogen detection sensor was manufactured in the same manner as in Example 1, except that a glass substrate was prepared as the sensor substrate.

Comparative Example

A color changeable hydrogen detection sensor was manufactured in the same manner as in Example 1, except that a coating layer for a hydrogen sensor, which was composed of a $WO_3$—Pd nanocomposite, was employed.

Experimental Example

Figure 6:
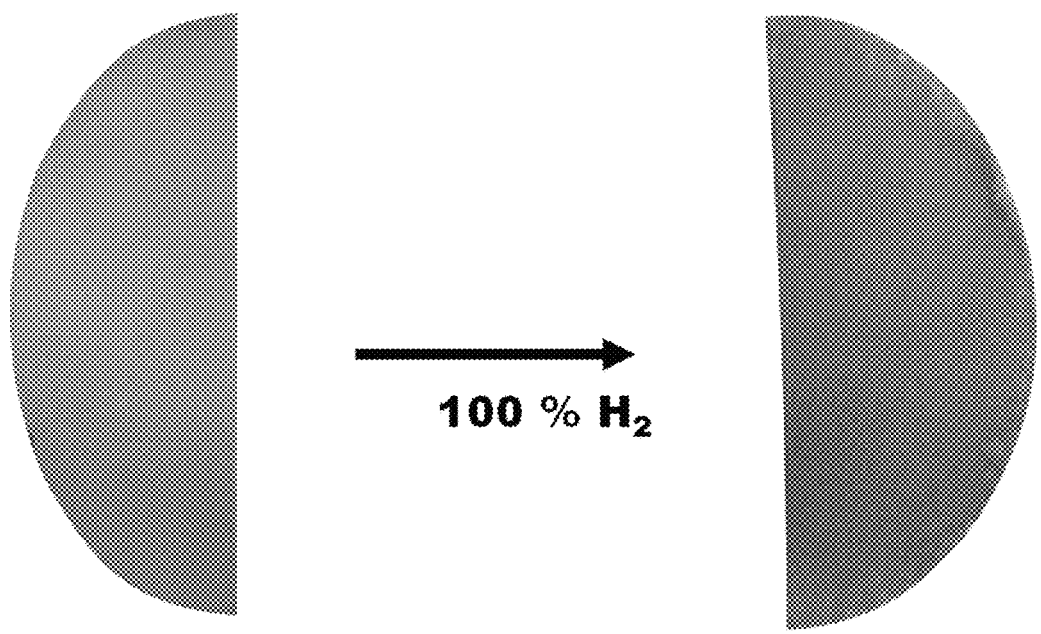
FIG. 6 shows a change in color of a paper filter manufactured in Example 1 according to an exemplary embodiment of the present invention.
Figure 7:
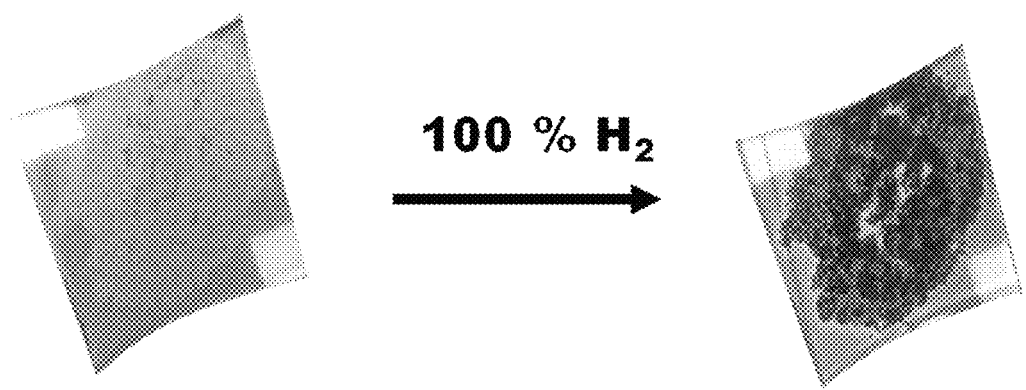
FIG. 7 shows a change in color of a glass substrate manufactured in Example 2 according to an exemplary embodiment of the present invention.

A hydrogen gas exposure test was evaluated by leaving the color changeable hydrogen detection sensors manufactured in Examples 1 and 2 and Comparative Example under the 100% hydrogen atmosphere for 5 hours in order to confirm hydrogen detection performance, and the results are shown in FIGS. 5, 6, and 7.

FIG. 6 is an image illustrating a change in color of the paper filter manufactured in Example 1. In FIG. 6, it was confirmed by the naked eye that the coating layer turned blue when a paper filter on which a coating layer for a hydrogen sensor, which was white color, had been coated was exposed to the 100% hydrogen atmosphere. Accordingly, it could be confirmed that the paper filter was exposed to hydrogen from the fact that the color of the paper filter was changed from white color to blue color.

FIG. 7 shows a change in color of the glass substrate manufactured in Example 2. In FIG. 7, it was confirmed that the surface of the glass substrate turned blue when a glass substrate, on which a coating layer for a hydrogen sensor, which was white color, had been coated was exposed to the 100% hydrogen atmosphere. As described above, it could be confirmed that the glass substrate was exposed to hydrogen from the change in the color of the glass substrate from white color to blue color.

Figure 8:
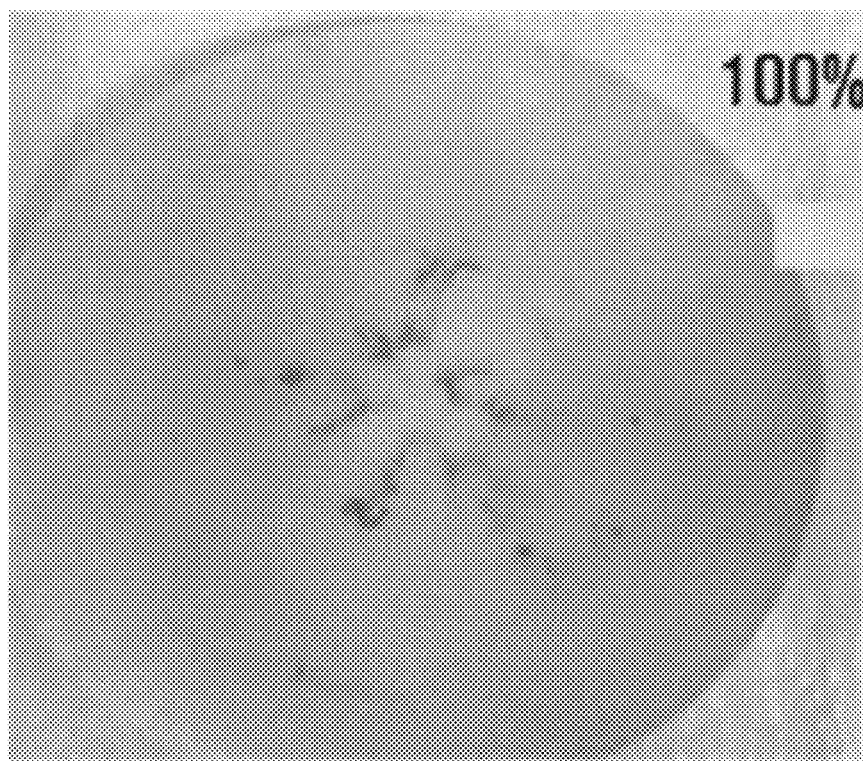
FIG. 8 shows a change in color of a paper filter manufactured in Comparative Example of the present invention.

FIG. 8 shows a change in color of the paper filter manufactured in Comparative Example. In FIG. 8, it was confirmed that the coating layer for a hydrogen sensor, which was composed of the $WO_3$—Pd nanocomposite, was grey color before being exposed to hydrogen, and partially was black color as in FIG. 8 after being exposed to hydrogen, but a clear change in color did not occur.

Therefore, in the color changeable hydrogen detection sensor manufactured in Examples 1 and 2, it was confirmed that the hydrogen sensing or sensitivity performance was excellent because a visible change in color before and after the sensors were exposed before and after exposure to hydrogen was obvious.

The invention has been described in detail with reference to various exemplary embodiments thereof. However, it will be appreciated by those skilled in the art that changes may be made in these embodiments without departing from the principles and spirit of the invention, the scope of which is defined in the appended claims and their equivalents.

What is claimed is:
1. A hydrogen detection sensor, comprising:
a substrate; and
a coating layer formed on a surface of the substrate and discolored when exposed to hydrogen,
wherein the coating layer comprises a molybdenum oxide ($MoO_3$)—Pd nanocomposite in which palladium (Pd) catalyst particles are adsorbed on an molybdenum oxide ($MoO_3$) nanostructure,
the molybdenum oxide ($MoO_3$)—Pd nanocomposite comprises the molybdenum oxide nanostructure and the palladium catalyst particles at a weight ratio of about 100:0.5 to 100:10.
2. The hydrogen detection sensor of claim 1, wherein the substrate is selected from the group consisting of a paper filter, a glass substrate, a polymer film, ink, pigment, and paint.

3. The hydrogen detection sensor of claim 1, wherein the molybdenum oxide ($MoO_3$) nanostructure has a length of about 1 to 100 μm and a diameter of about 20 to 100 nm.

4. The hydrogen detection sensor of claim 1, wherein the palladium (Pd) catalyst particles have an average particle diameter of about 3 to 15 nm.

5. The hydrogen detection sensor of claim 1, wherein the coating layer has a coating thickness of about 0.1 to 200 μm.

6. A vehicle comprising a hydrogen detection sensor of claim 1.

7. A method of manufacturing a hydrogen detection sensor-, comprising the steps of:
providing a substrate;
forming a molybdenum oxide nanostructure;
preparing a palladium catalyst solution by mixing a polymer with a palladium precursor solution;
forming an $MoO_3$—Pd nanocomposite by mixing the molybdenum oxide nanostructure with the palladium catalyst solution and irradiating UV light to the mixture; and
forming a coating layer by coating the $MoO_3$—Pd nanocomposite on the substrate,
wherein the $MoO_3$—Pd nanocomposite comprises the molybdenum oxide nanostructure and the palladium catalyst particles at a weight ratio of about 100:05 to 100:10.

8. The method of claim 7, wherein step of forming the molybdenum oxide nanostructure comprises:
preparing an aqueous molybdenum oxide solution by mixing an acid solution with an aqueous molybdenum ammonium solution;
forming the molybdenum oxide nanostructure by hydrothermally synthesizing the aqueous molybdenum oxide solution; and
heat-treating the molybdenum oxide nanostructure.

9. The method of claim 8, wherein the molybdenum oxide nanostructure is formed at a temperature of about 140 to 180° C. for about 2 to 6 hours.

10. The method of claim 8, wherein the molybdenum oxide nanostructure is heat-treated at a temperature of about 400 to 600° C. for about 1 to 3 hours.

11. The method of claim 7, wherein the polymer is polyvinylpyrrolidone, polyvinyl alcohol, or a mixture thereof.

* * * * *